United States Patent [19]

Sato

[11] Patent Number: 5,597,938
[45] Date of Patent: Jan. 28, 1997

[54] PROCESS FOR PRODUCING INTERMEDIATE FOR 13,14-DIDEHYDROPROSTAGLANDIN E

[75] Inventor: Fumie Sato, 1-219, Kugenumahigashi 3-chome, Fujisawa-shi, Kanagawa, Japan

[73] Assignees: Taisho Pharmaceutical Co., Ltd.; Fumie Sato, both of Japan

[21] Appl. No.: 505,165

[22] PCT Filed: Feb. 17, 1994

[86] PCT No.: PCT/JP94/00243

§ 371 Date: Aug. 10, 1995

§ 102(e) Date: Aug. 10, 1995

[87] PCT Pub. No.: WO94/19319

PCT Pub. Date: Sep. 1, 1994

[30] Foreign Application Priority Data

Feb. 19, 1993 [JP] Japan ................................. 5-030199

[51] Int. Cl.$^6$ .......................... C07F 7/08; C07F 7/10; C07F 7/18
[52] U.S. Cl. ...................... 556/436; 556/413; 556/415; 556/428; 556/437; 549/214; 549/415; 549/416; 549/419; 549/420; 549/421; 549/505; 560/125; 560/126; 562/503; 568/379
[58] Field of Search ..................... 556/436, 437, 556/413, 415, 428; 549/214, 415, 416, 419, 420, 421, 505; 560/125, 126; 562/503; 568/379

[56] References Cited

U.S. PATENT DOCUMENTS

| 4,778,904 | 10/1988 | Cooper | 549/415 |
| 5,254,708 | 10/1993 | Sato et al. | 556/436 |
| 5,283,349 | 1/1994 | Tanaka et al. | 556/436 |
| 5,380,900 | 1/1995 | Sato et al. | 556/436 |

FOREIGN PATENT DOCUMENTS 0591532 4/1992 European Pat. Off. .
0597095 4/1992 European Pat. Off. .
58-198466 11/1983 Japan .
1-228936 9/1989 Japan .
5-117230 5/1993 Japan .

*Primary Examiner*—Paul F. Shaver
*Attorney, Agent, or Firm*—Lorusso & Loud

[57] ABSTRACT

A novel process for the production of a compound represented by the formula:

$$\text{ZO} \overset{O}{\underset{\underset{C-(CH_2)_s-\underset{OZ'}{\overset{R^1}{\underset{|}{C}}}-R^2}{\|\|}}{\bigtriangleup}} CH_2(CR^3R^4)_m A_n (CH_2)_p X_q (CHR^5)_r R^6$$

wherein Z and Z' each represents a protective group for the hydroxyl group; $R^1$ represents a hydrogen atom or an alkyl group; $R^2$ represents an alkyl group, a cycloalkyl group, an alkenyl group, an alkynyl group, a group represented by the formula —B—D (in which B is an alkylene group and D is a substituted or unsubstituted phenyl group, a substituted or unsubstituted phenoxy group or a cycloalkyl group), a substituted or unsubstituted phenyl group or a substituted or unsubstituted phenoxy group; $R^3$ and $R^4$ each represents a hydrogen atom, an alkyl group or an alkoxy group; $R^5$ represents a hydrogen atom, an alkyl group, an alkoxy group, a halogen atom, a cyano group, an amino group, a hydroxyl group or a group represented by a formula —COOR$^8$; $R^6$ represents a group represented by a formula —COOR$^9$, a cyano group, a hydroxyl group, a group represented by a formula —OCOR$^{10}$ or a group represented by a formula —CONR$^{11}$R$^{12}$; A represents a vinylene group, an ethynylene group, a phenylene group or a group represented by a formula —C=C=C—; X represents an oxygen atom or a sulfur atom; m represents an integer of 0 to 7; n is 0 or 1; each of p and r is an integer of 0 to 5; q is 0 or 1; and s is 0 or 1.

4 Claims, No Drawings

PROCESS FOR PRODUCING INTERMEDIATE FOR 13,14-DIDEHYDROPROSTAGLANDIN E

This application is a 371 of PCT/JP94/00243 filed Feb. 17, 1994.

TECHNICAL FIELD

This invention relates to a process for producing an intermediate for the synthesis of a 13,14-didehydroprostaglandin (hereinafter referred to as 13,14-didehydro PG) E useful as various medicines.

BACKGROUND ART

As the most useful process for the production of a 13,14-didehydro PGE among the prior art processes, a process is disclosed on pages 3 and 4 of WO 92/18472, in which the α-chain of PG is introduced by a conjugated addition reaction using an organic copper compound.

However, since the above process is an anionic reaction, an organic copper compound, which has a reactive hydrogen atom-containing substituent such as free carboxyl group, cannot be used in the reaction. Also, because of an anionic reaction, the organic copper compound cannot be prepared easily and a side reaction is apt to occur at the time of the s-chain introduction, when the starting material is a compound which contains the following groups and the like as its partial structure;

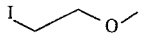

which is apt to cause β-elimination;

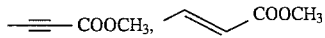

which is apt to cause Michael addition: or

which easily becomes allene. Further, this process has another disadvantages in that it is necessary to prevent contamination of water and oxygen when the α-chain is introduced and it generally requires a very low temperature. In addition, it requires a number of steps after introduction of the α-chain until its final step.

The object of the present invention is to resolve the aforementioned problems involved in the prior art and hence to provide a process for the production of intermediates for use in the production of an industrially advantageous 13,14-didehydro PGE.

DISCLOSURE OF THE INVENTION

Accordingly, the present invention relates to a process for the production of an intermediate for a 13,14-didehydroprostaglandin E, represented by the following formula (I)

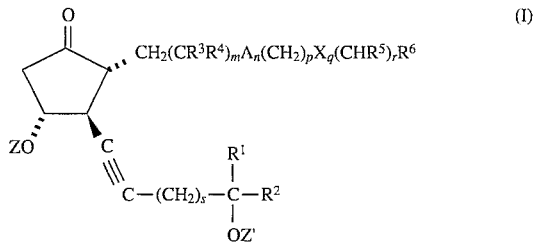

wherein Z and Z' each represents a protective group for the hydroxyl group; $R^1$ represents a hydrogen atom or an alkyl group having 1 to 4 carbon atoms; $R^2$ represents an alkyl group having 1 to 10 carbon atoms, a cycloalkyl group having 3 to 8 carbon atoms, an alkenyl group having 2 to 10 carbon atoms, an alkynyl group having 2 to 10 carbon atoms, a group represented by the formula —B—D (in which B represents an alkylene group having 1 to 4 carbon atoms and D represents a phenyl group, a phenoxy group, a phenyl group substituted with "a halogen atom, a trifluoromethyl group, an alkyl group having 1 to 6 carbon atoms, an alkoxy group having 1 to 6 carbon atoms, a phenyl group or a phenoxy group", a phenoxy group substituted with "a halogen atom, a trifluoromethyl group, an alkyl group having 1 to 6 carbon atoms, an alkoxy group having 1 to 6 carbon atoms, a phenyl group or a phenoxy group" or a cycloalkyl group having 5 to 7 carbon atoms), a phenyl group, a phenoxy group, a phenyl group substituted with "a halogen atom, a trifluoromethyl group, an alkyl group having 1 to 6 carbon atoms or an alkoxy group having 1 to 6 carbon atoms" or a phenoxy group substituted with "a halogen atom, a trifluoromethyl group, an alkyl group having 1 to 6 carbon atoms or an alkoxy group having 1 to 6carbon atoms"; $R^3$ and $R^4$ each represents a hydrogen atom, an alkyl group having 1 to 4 carbon atoms or an alkoxy group having 1 to 4 carbon atoms; $R^5$ represents a hydrogen atom, an alkyl group having 1 to 6 carbon atoms, an alkoxy group having 1 to 6 carbon atoms, a halogen atom, a cyano group, an amino group, a hydroxyl group or a group represented by a formula —$COOR^8$ (in which $R^8$ represents a hydrogen atom, an alkyl group having 1 to 6 carbon atoms or an alkenyl group having 2 to 6 carbon atoms); $R^6$ represents a group represented by a formula —$COOR^9$ (in which $R^9$ represents a hydrogen atom, an alkyl group having 1 to 6 carbon atoms or an alkenyl group having 2 to 6 carbon atoms), a cyano group, a hydroxyl group, a group represented by a formula —$OCOR^{10}$ (in which $R^{10}$ represents a hydrogen atom, an alkyl group having 1 to 6 carbon atoms or an alkenyl group having 2 to 6 carbon atoms) or a group represented by a formula —$CONR^{11}R^{12}$ (in which $R^{11}$ and $R^{12}$ each represents a hydrogen atom, an alkyl group having 1 to 6 carbon atoms or a phenyl group); A represents a vinylene group, an ethynylene group, a phenylene group or a group represented by a formula —C=C=C—; X represents an oxygen atom or a sulfur atom; m is an integer of 0 to 7; n is 0 or 1; each of p and r is an integer of 0 to 5; q is 0 or 1; and s is 0 or 1, with the proviso that the total number of straight chain carbon atoms of the α-chain in the formula is within the range of from 4 to 10, which comprises allowing a compound represented by the formula (II)

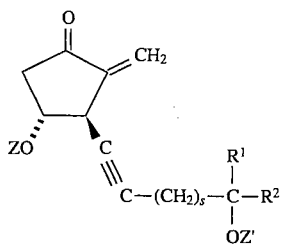

(II)

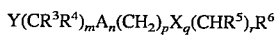

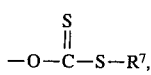

(wherein Z, Z', $R^1$, $R^2$ and s are as defined above) to undergo a radical reaction with a compound represented by the formula (III)

$$Y(CR^3R^4)_m A_n (CH_2)_p X_q (CHR^5)_r R^6 \quad (III)$$

(wherein Y represents a halogen atom or a group represented by the formula $$-O-\overset{S}{\underset{\|}{C}}-S-R^7,$$

in which $R^7$ represents a hydrogen atom, an alkyl group having 1 to 9 carbon atoms or a phenyl group; and $R^3$, $R^4$, $R^5$, $R^6$, A, X, m, n, p, q and r are as defined above) using a radical generator.

According to the present invention, examples of the protective group for the hydroxyl group include those which are usually used in the field of PG, such as trialkylsilyl group (e.g., t-butyldimethylsilyl group, trimethylsilyl group, triethylsilyl group, phenyldimethylsilyl group or t-butyldiphenylsilyl group), tetrahydropyranyl (THP) group, tetrahydrofuranyl group, alkoxyalkyl groups (e.g., methoxymethyl group or ethoxyethyl group), benzyloxymethyl group, benzyl group and trityl group.

The alkyl group, alkoxy group, alkenyl group or alkylene group means a straight- or branched-chain group. The halogen atom means fluorine atom, chlorine atom, bromine atom or iodine atom.

Next, illustrative examples of the compound of formula (III) are shown below [examples of $R^{13}$ when the compound of formula (III) is expressed as $YR^{13}$ (wherein Y is as defined above].

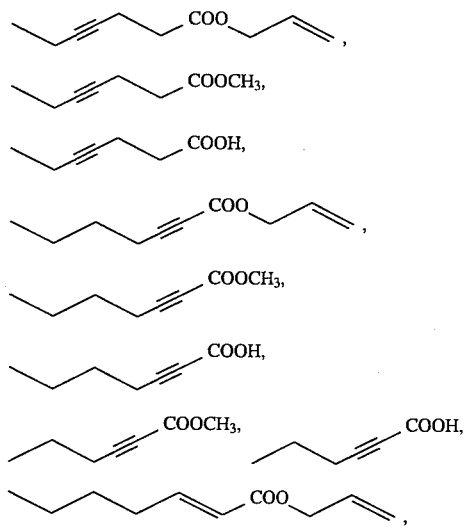

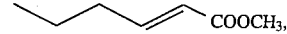
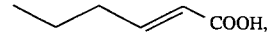
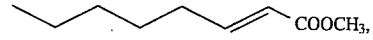
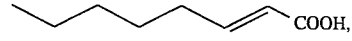
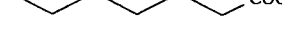
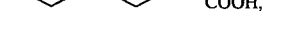
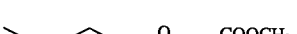
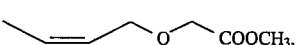
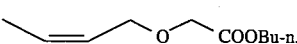
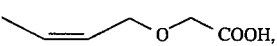
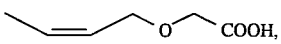

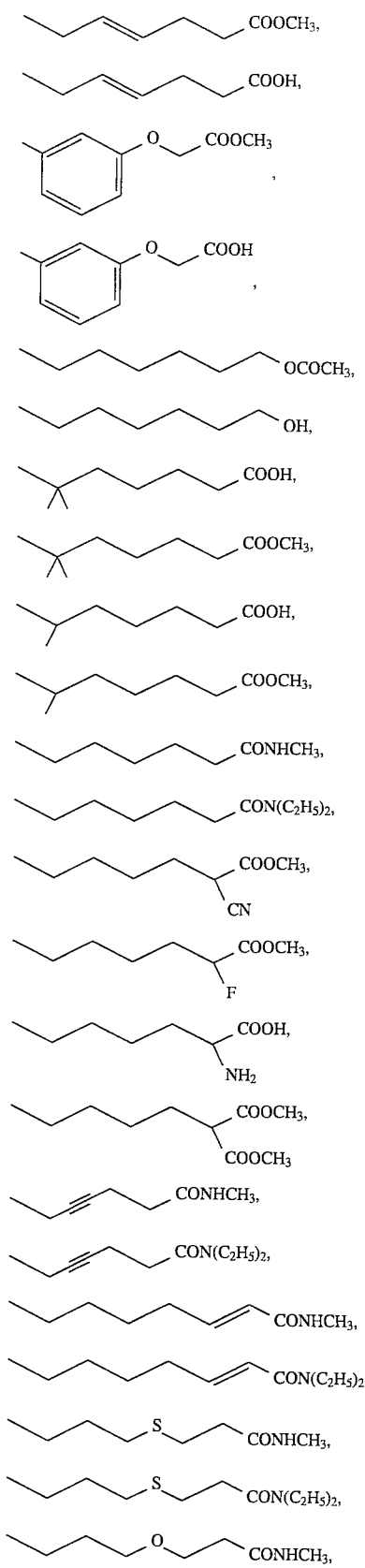

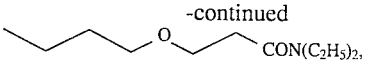

The production process of the present invention is now described in detail below.

Firstly, in the reaction of the compound of formula (II) with the compound of formula (III), the compound of formula (III) is used in an amount of from 0.5 to 10 equivalents, preferably from 1 to 5 equivalents, based on the compound of formula (II).

The radical generator is used as a radical initiation catalyst, and examples of the radical generator include peroxides such as benzoyl peroxide, acetyl peroxide, t-butyl hydroperoxide, cumene hydroperoxide and potassium peroxodisulfate, azo compounds such as azobisisobutyronitrile and azobiscyclohexanecarbonitrile, alkylborane compounds such as trimethylborane, triethylborane and tributylborane, or a "zinc powder treated with a copper salt or an ammonium salt by ultrasonic wave".

When a peroxide, an azo compound or an alkylborane compound is used as the radical generator, it is used in an amount of from its catalytically effective amount to several equivalents, preferably from 0.05 to 2 equivalents, based on the compound of formula (III). In that case, it is desirable to use as a radical reducing agent (iodine scavenger) a tin hydride compound such as tributyltin hydride, triphenyltin hydride, dibutyltin hydride and diphenyltin hydride in an amount of from 0 to excess, preferably from 1 to 5 equivalents, based on the compound of formula (III). The aforementioned reaction can be carried out using a solvent, and examples of the solvent include those which do not participate in the reaction, such as benzene, toluene, xylene, cyclohexane, hexane and pentane, which may be used alone or as a mixture thereof. The reaction temperature is generally within the range of from −100° C. to a reflux temperature of the solvent, preferably from −50° to 100° C. When an alkylborane compound is particularly used as the radical generator, the reaction progresses even at a low temperature. The reaction time is generally from 10 minutes to 24 hours.

In addition, when the "zinc powder treated with a copper salt or an ammonium salt by ultrasonic wave" is used as the radical generator, copper iodide, copper bromide, copper chloride or the like can be used as the copper salt, or ammonium chloride, ammonium acetate, ammonium sulfate, tetramethylammonium chloride, tetraethylammonium bromide or the like can be used as the ammonium salt, and, in that case, excess amount, preferably 1 to 5 equivalents, of zinc and catalytically effective amount, preferably 0.05 to 2 equivalents of the copper salt or ammonium salt may be used based on the compound of formula (III). As the reaction solvent, water, alcohols such as methanol, ethanol, isopropanol and butanol, ethers such as ether, tetrahydrofuran and dioxane and polar solvents such as acetonitrile, N,N-dimethylformamide and dimethylsulfoxide may be used alone or as a mixture thereof. The reaction temperature is within the range of from −20° to 80° C., preferably from 10° to 25° C., and the reaction time is 30 minutes to 24 hours.

When Y in the formula (III) is a group represented by the formula

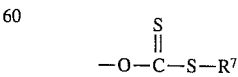

in which $R^7$ is as defined above, such a compound can be synthesized from its corresponding alcohol compound (a compound of formula (III) in which a portion corresponding to Y is a hydroxyl group) in accordance with a known method (for example, D. H. R. Barton et al., *Synthesis*, 1981, 743).

The thus-obtain compound of formula (I) can be introduced easily into a 13,14-didehydro PGE or analogues thereof, which are useful as various medicines, by a conventional method deprotecting the protective group for the hydroxyl group.

INDUSTRIAL APPLICABILITY

The present invention has rendered possible production of a compound as an important intermediate for the 13,14-didehydro PGE useful as various medicines, with a high yield by few production steps under neutral and mild conditions, without requiring preparation of unstable anionic reagents and prevention of water and oxygen contamination at the time of the reaction and without causing formation of by-products by the reaction. In other words, it has rendered possible industrially advantageous production of the compound of formula (I).

BEST MODE OF CARRYING OUT THE INVENTION

The following examples are provided to further illustrate the present invention in greater detail.

INVENTIVE EXAMPLE 1

Production of (17S)-17,20-dimethyl-4,4,5,5,13,14-hexadehydro-PGE$_1$ allyl ester 11,15-bis(t-butyldimethylsilyl ether)

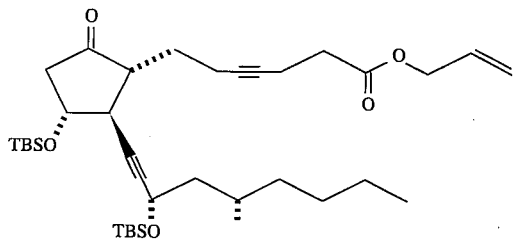

In an atmosphere of argon, tributyltin hydride (1.08 ml) and azobisisobutyronitrile (8.2 mg) were added at room temperature to a benzene (10 ml) solution containing (3R, 4R)-2-methylene-3-[(3'S,5'S)-3'-(t-butyldimethylsiloxy)-5'-methylnon-1'-ynyl]-4-(t-butyldimethylsiloxy)cyclopentan-1-one (493 mg) and 6-iodo-4-hexynoic acid allyl ester (1.11 g), and the mixture was stirred for 2 hours at 80° C.

The reaction solution was cooled, passed through a short column packed with silica gel, concentrated under a reduced pressure, and then purified by a silica gel column chromatography to give 217 mg of the title compound.

$^1$H (CDCl$_3$, 300 MHz) δ (ppm);
  0.09, 0.11 and 0.14 (3s, 12H), 0.89 and 0.90 (2s, 18H), 0.80–0.97 (m, 6H), 1.02–2.00 (m, 11H), 2.19 (dd, J =6.9Hz, 18.3Hz, 1H), 2.24–2.37 (m, 3H), 2.41–2.56 (m, 4H), 2.62–2.76 (m, 2H), 4.24–4.34 (m, 1H), 4.42 (dt, J =1.4Hz, 6.9Hz, 1H), 4.59 (dt, J =5.7Hz, 1.4Hz, 2H), 5.23 (ddt, J =1.3Hz, 10.4Hz, 1.2Hz, 1H), 5.32 (ddt, J =1.5Hz, 17.2Hz, 1.5Hz, 1H), 5.91 (ddt, J =10.4Hz, 17.2Hz, 5.7Hz, 1H)

$^{13}$C-NMR (CDCl$_3$, 75 MHz) δ (ppm); –4.9, –4.8, –4.6, –4.3, 14.2, 14.8, 16.7, 18.0, 18.2, 20.0, 23.0, 25.7, 25.8, 28.6, 29.1, 29.4, 33.9, 36.4, 42.3, 46.2, 47.1, 53.7, 61.6, 65.2, 73.5, 79.0, 80.0, 83.6, 85.2, 118.1, 132.1, 171.6, 214.5

INVENTIVE EXAMPLE 2

Production of 16-henox-17,18,19,20-tetranor-4,4,5,5,13,14-hexadehydro-PGE$_1$ methyl ester 11,15-bis(t-butyl-dimethylsilyl ether)

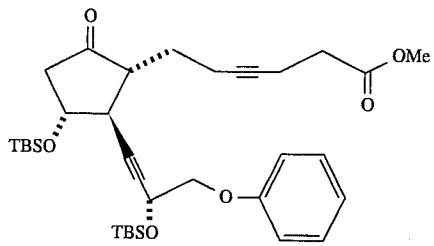

In an atmosphere of argon, tributyltin hydride (1.08 ml) and triethylborane (2.0M, hexane solution, 50 μg) were added at 0° C. to a toluene (1 ml) solution containing (3R,4R)-2-methylene-3-[(3'R)-3'-(t-butyldimethylsiloxy)-4'-phenoxybut-1'-ynyl]-4-(t-butyldimethylsiloxy)cyclopentan-1-one (500.8 mg) and 6-iodo-4-hexynoic acid methyl ester (1.01 g), and the mixture was stirred for 4 hours at the same temperature.

The reaction solution was passed through a short column packed with silica gel, concentrated under a reduced pressure, and then purified by a silica gel column chromatography to give 285 mg of the title compound.
$^1$H-NMR (CDCl$_3$, 300 MHz) δ (ppm);
  0.06 and 0.12 (2s, 12H), 0.89 and 0.91 (2s, 18H), 1.70–1.86 (m, 1H), 1.86–2.01 (m, 1H), 2.29 (dd, J =9.1Hz, 18.5Hz, 1H), 2.30–2.54 (m, 7H), 2.70–2.84 (m, 2H), 3.69 (s, 3H), 4.09 (dd, J =7.0Hz, 9.7 Hz, 1H), 4.15 (dd, J =9.7Hz, 3.9Hz, 1H), 4.28–4.42 (m, 1H), 4.75–4.85 (m, 1H), 6.90–7.05 (m, 3H), 7.24–7.36 (m, 2H)

INVENTIVE EXAMPLE 3

Production of 15-cyclohexyl-16,17,18,19,20-pentanol-13,14-didehydro-PGE$_1$ allyl ester 11,15-bis(t-butyldimethylsilyl ether)

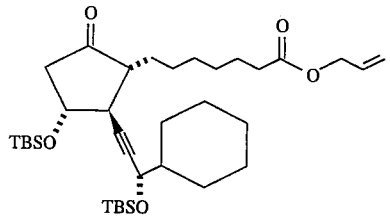

A suspension of zinc powder (584 mg) and copper(I) iodide (357 mg) in diethyl ether-water (9:1) (16.3 ml) were treated with ultrasonic wave for 5 minutes, a diethyl ether-water (9:1) (4 ml) solution containing (3R,4R)-2-methylene-3-[(3'S)-3'-(t-butyldimethylsiloxy)-3'-cyclohexylprop-1'-ynyl]-4-(t-butyldimethylsiloxy)cyclopentan-1-one (476.9 mg) and 6-iodo-4-hexanoic acid allyl ester (1.13 g) was added thereto, and the mixture was subjected to ultrasonic treatment for 6 hours at 18° C. The reaction solution was mixed with saturated aqueous sodium chloride solution (15 ml), extracted with ether, dried and concentrated in the conventional method, and then purified by a silica gel column chromatography to obtain 310 mg of the title compound.

$^1$H-NMR (CDCl$_3$, 300 MHz) δ (ppm);

0.05, 0.07 and 0.09 (38, 12H), 0.88 and 0.89 (28, 18H), 1.00–1.90 (m, 21H), 2.12–2.26 (m, 2H), 2.32 (t, J =7.5Hz, 2H), 2.58–2.73 (m, 2H), 4.08 (dd, J =1.5Hz, 6.3Hz, 1H), 4.24–4.33 (m, 1H), 4.57 (d, J =5.7Hz, 2H), 5.20–5.36 (m, 2H), 5.83–5.99 (m, 1H)

The following compounds were obtained substantially in the same manner as Inventive Examples 1 to 3.

(16S)-15-Dehydroxy-16-hydroxy-16-methyl-13,14-didehydro-PGE$_1$ methyl ester 11,16-bis(t-butyldimethylsilyl ether)

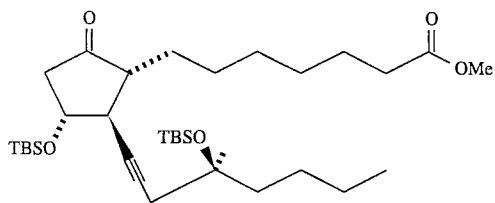

$^1$H-NMR (CDCl$_3$, 300 MHz) δ (ppm);

0.09 and 0.12 (2s, 6H), 0.57 (q, J =7.7Hz, 6H), 0.80–1.00 (m, 3H), 0.89 (s, 9H), 0.94 (t, J =7.7Hz, 9H), 1.20–1.80 (m, 16H), 1.26 (s, 3H), 2.09–2.22 (m, 1H), 2.16 (dd, J =7.0Hz, 18.0Hz, 1H), 2.22–2.42 (m, 2H), 2.29 (t, J =7.5Hz, 2H), 2.59–2.71 (m, 1H), 2.65 (dd, J =6.8Hz, 18.0 Hz, 1H), 3.66 (s, 3H), 4.21–4.31 (m, 1H)

(16R)-15-Dehydroxy-16-hydroxy-16-methyl-13,14-didehydro-PGE$_1$ methyl ester 11,16-bis(t-butyldimethylsilyl ether)

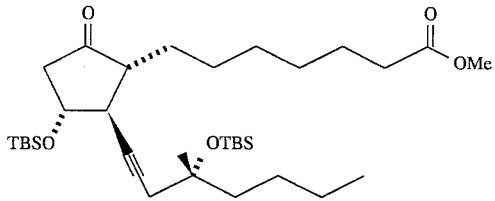

$^1$H-NMR (CDCl$_3$, 300 MHz) δ (ppm);

0.08 and 0.12 (2s, 6H), 0.57 (q, J =7.5Hz, 6H), 0.89 (s, 9H), 0.95 (t, J =7.5Hz, 9H), 0.92–0.99 (m, 3H), 1.20–1.80 (m, 16H), 1.27 (s, 3H), 2.16 (dd, J =6.9Hz, 18.2Hz, 1H), 2.10–2.22 (m, 1H), 2.22–2.37 (m, 2H), 2.29 (t, J =7.5Hz, 2H), 2.60–2.70 (m, 1H), 2.65 (dd, J =6.6Hz, 18.2Hz, 1H), 3.66 (s, 3H), 4.22–4.30 (m, 1H)

What is claimed is:

1. A process for producing an intermediate for a 13,14,-didehydroprostaglandin E, represented by the formula:

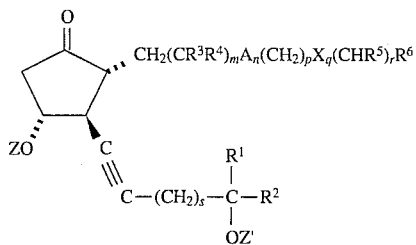

wherein Z and Z' and represents a protective group for the hydroxyl group; R$^1$ represents a hydrogen atom or an alkyl group having 1 to 4 carbon atoms; R$^2$ represents an alkyl group having 1 to 10 carbon atoms, a cycloalkyl group having 3 to 8 carbon atoms, an alkenyl group having 2 to 10 carbon atoms, an alkynyl group having 2 to 10 carbon atoms, a group represented by the formula —B—D (in which B represents an alkylene group having 1 to 4 carbon atoms and D represents a phenyl group, a phenoxy group, a phenyl group substituted with "a halogen atom, a trifluoromethyl group, an alkyl group having 1 to 6 carbon atoms, an alkoxy group having 1 to 6 carbon atoms, a phenyl group or a phenoxy group", a phenoxy group substituted with "a halogen atom, a trifluoromethyl group, an alkyl group having 1 to 6 carbon atoms, an alkoxy group having 1 to 6 carbon atoms, a phenyl group or a phenoxy group" or a cycloalkyl group having 5 to 7 carbon atoms), a phenyl group, a phenoxy group, a phenyl group substituted with "a halogen atom, a trifluoromethyl group, an alkyl group having 1 to 6 carbon atoms or an alkoxy group having 1 to 6 carbon atoms" or a phenoxy group substituted with "a halogen atom, a trifluoromethyl group, an alkyl group having 1 to 6 carbon atoms or an alkoxy group having 1 to 6 carbon atoms"; R$^3$ and R$^4$ each represents a hydrogen atom, an alkyl group having 1 to 4 carbon atoms or an alkoxy group having 1 to 4 carbon atoms; R$^5$ represents a hydrogen atom, an alkyl group having 1 to 6 carbon atoms, an alkoxy group having 1 to 6 carbon atoms, a halogen atom, a cyano group, an amino group, a hydroxyl group or a group represented by a formula —COOR$^8$ (in which R$^8$ represents a hydrogen atom, an alkyl group having 1 to 6 carbon atoms or an alkenyl group having 2 to 6 carbon atoms); R$^6$ represents a group represented by a formula —COOR$^9$ (in which R$^9$ represents a hydrogen atom, an alkyl group having 1 to 6 carbon atoms or an alkenyl group having 2 to 6 carbon atoms), a cyano group, a hydroxyl group, a group represented by a formula —OCOR$^{10}$ (in which R$^{10}$ represents a hydrogen atom, an alkyl group having 1 to 6 carbon atoms or an alkenyl group having 2 to 6 carbon atoms) or a group represented by a formula —CONR$^{11}$R$^{12}$ (in which R$^{11}$ and R$^{12}$ each represents a hydrogen atom, an alkyl group having 1 to 6 carbon atoms or a phenyl group); A represents a vinylene group, an ethynylene group, a phenylene group or a group represented by a formula —C=C=C—; X represents an oxygen atom or a sulfur atom; m is an integer of 0 to 7; n is 0 or 1; each of p and r is an integer of 0 to 5; q is 0 or 1; and s is 0 or 1, with the proviso that the total number of straight chain carbon atoms of the s-chain in the formula is within the range of from 4 to 10, which comprises allowing a compound represented by the formula:

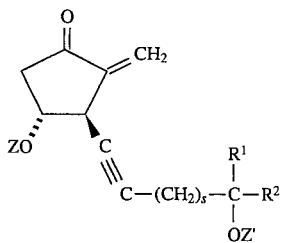

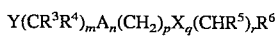

(wherein Z, Z', $R^1$, $R^2$ and s are as defined above) to undergo a radical reaction with a compound represented by the formula:

$$Y(CR^3R^4)_m A_n (CH_2)_p X_q (CHR^5)_r R^6$$

(wherein Y represents a halogen atom or a group represented by the formula

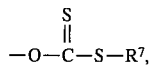

in which $R^7$ represents a hydrogen atom, an alkyl group having 1 to 9 carbon atoms or a phenyl group, and $R^3$, $R^4$, $R^5$, $R^6$, A, X, m, n, p, q and r are as defined above) using a radical generator.

2. The process according to claim 1, wherein the radical generator is a peroxide, an azo compound or an alkylborane compound.

3. The process according to claim 2, wherein the reaction is carried out using a tin hydride compound together with the radical generator.

4. The process according to claim 1, wherein the radical generator is a "zinc powder treated with a copper salt or an ammonium salt by ultrasonic wave".

* * * * *

UNITED STATES PATENT AND TRADEMARK OFFICE
CERTIFICATE OF CORRECTION

PATENT NO. : 5,597,938
DATED : January 28, 1997
INVENTOR(S) : Fumie SATO

It is certified that error appears in the above-indentified patent and that said Letters Patent is hereby corrected as shown below:

Col. 1, line 32, "s-chain" should read --$\alpha$-chain--.

Col. 2, line 36, "6carbon" should read --6 carbon--.

Col. 8, line 9, "henox" should read --phenoxy--.

Col. 9, line 9, "38" should read --$3s$-- and "28" should read --$2s$--.

Col. 10, line 65, "s-chain" should read --$\alpha$-chain--.

Signed and Sealed this

Ninth Day of December, 1997

Attest:

BRUCE LEHMAN

Attesting Officer

Commissioner of Patents and Trademarks